United States Patent [19]

Greenberg et al.

[11] Patent Number: 5,780,039
[45] Date of Patent: Jul. 14, 1998

[54] ORALLY-INGESTIBLE NUTRITION COMPOSITIONS HAVING IMPROVED PALATABILITY

[75] Inventors: Norman A. Greenberg, New Hope; Candis Kvamme, Brooklyn Park; Mary K. Schmidl, Arden Hills, all of Minn.

[73] Assignee: Novartis Nutrition AG, Basel, Switzerland

[21] Appl. No.: 872,870

[22] Filed: Apr. 23, 1992

[51] Int. Cl.$^6$ .................................................. A61K 9/00
[52] U.S. Cl. .................. 424/400; 424/455; 424/489; 426/98; 426/534; 426/656; 426/800; 426/801
[58] Field of Search .................. 426/656, 98, 534, 426/800, 801; 424/400, 455, 489

[56] References Cited

U.S. PATENT DOCUMENTS

| | | | |
|---|---|---|---|
| 3,897,361 | 7/1975 | Saeki et al. | 264/4.3 |
| 3,950,547 | 4/1976 | Lamar | 426/656 |
| 4,064,138 | 12/1977 | Saari | 562/560 |
| 4,414,238 | 11/1983 | Schmidl | 426/602 |
| 4,420,432 | 12/1983 | Chibata et al. | 562/562 |
| 4,752,618 | 6/1988 | Mascioli et al. | 514/549 |
| 4,758,553 | 7/1988 | Ogoshi et al. | 514/47 |
| 4,820,731 | 4/1989 | Mascioli et al. | 514/549 |
| 4,871,768 | 10/1989 | Bistrian et al. | 514/547 |
| 4,959,350 | 9/1990 | Frokjaer | 426/656 |
| 4,981,844 | 1/1991 | Alexander et al. | 514/21 |
| 5,053,387 | 10/1991 | Alexander | 514/2 |
| 5,066,500 | 11/1991 | Gil | 426/801 |

Primary Examiner—D. Gabrielle Brouillette
Attorney, Agent, or Firm—Michael P. Morris

[57] ABSTRACT

An orally-ingestible nutrition composition having improved taste comprises a low pH (<7.0) form of an amino acid selected from arginine, valine and compounds associated with the synthesis of polyamines. Preferred low pH forms are salts such as arginine phosphate and mixtures thereof with arginine citrate. Preferred nutrition composition also comprise encapsulated polyunsaturated fatty acid.

12 Claims, No Drawings

5,780,039

ORALLY-INGESTIBLE NUTRITION COMPOSITIONS HAVING IMPROVED PALATABILITY

BACKGROUND OF THE INVENTION

Greater and greater attention is being given to nutrition and its critical role in health and in fighting diseases and other infections. A variety of nutritional compositions have been administered in the past to hospitalized patients, particularly critically ill patients, to stimulate the immune system and minimize the risk of infections. The prior art has shown that nutritional adjunctive therapy given to patients either enterally or parenterally is efficacious in reversing catabolism and stimulating anabolism. This improvement in the metabolic state of the patient is believed to be critical to the healing process and patient survival.

Surgical procedures are an extreme assault upon the body and can affect the immune response system of the patient. It has been shown that nutrition can also affect the immune response system after surgery or other major assaults to the body. For example, U.S. Pat. No. 4,981,844 describes a method to improve immune response and resistance to infection by administering to a patient, for at least 10 days prior to surgery, a diet having 20–60 kilocalories per kilogram body weight wherein 20–80% of the calories are derived from linoleic acid.

U.S. Pat. No. 4,752,618 discloses a method of minimizing infections by administering a diet rich in omega-3 fatty acids. U.S. Pat. No. 4,758,553 describes compositions of nucleic acid components for nutritional replenishment which enhances the efficient use of the amino acids in the body and assures nutrition control and nitrogen balance.

U.S. Pat. No. 4,820,731 disclosed a parenteral dietary supplement which minimizes the risk of infection containing a mixture of oils rich in omega-3 and omega-6 fatty acids. U.S. Pat. No. 4,871,768 describes a dietary supplement containing omega-3 oils and medium chain triglycerides. U.S. Pat. No. 5,053,387 describes compositions for treating a traumatic injury comprising an intact protein, arginine, carbohydrate, lipid comprising the omega-3 fatty acids of fish oil and linoleic acid.

U.S. Pat. No. 4,414,238 discloses a liquid elemental diet comprising carbohydrate, amino acid, and lipid components having a pH ranging from about 3.0 to 4.4.

U.S. Pat. No. 4,420,432 describes neutral crystalline salts of basic L-amino acid with L-malic acid.

European Patent Publication No. 0246747 describes an enteral diet product with a pH lower than about 4.5 and comprising protein or protein derived compounds, fat, carbohydrate and water.

U.S. Pat. No. 4,417,916 describes the encapsulation of a wide variety of pharmaceuticals, flavoring materials and the like. U.S. Pat. No. 3,897,361 describes a process for producing microcapsules of hydrophobic oils such as mineral oils, fish oils, vegetable oils and the like.

Of the three major routes available for nutrition support of hospitalized patients (i.e. oral, gastrointestinal and intravenous), the oral route is the most underutilized. Nutrition support by the oral route requires that the voluntary ingestion of foodstuffs not only meet recommended dietary allowances, but also correct prior deficiencies and meet the additional metabolic requirements of disease or trauma. The hedonic (like-dislike) response of the individual to the flavor of the food to be ingested is an important determinant of whether it will be consumed and in what quantity. Flavor broadly defined includes smell and taste (flavor is modified by texture and temperature).

A number of factors contribute to the unpleasant flavors of most nutrition support compositions. These include: (1) bitter-tasting amino acids such as arginine; (2) fish oils; (3) thermoprocessing of the compositions; and (4) the protein source such as casein. To make a good tasting product, a number of problems had to be solved with the present invention through novel techniques and combinations of components. At normal alkaline pH, arginine and other amino acids have an extremely bitter, off flavor that is extremely undesirable. Fish oils are known for their objectionable taste and organoleptic properties. Thermoprocessing of liquid nutrition composition can lead to unpalatable decomposition by-products. Coagulation problems can result from the use of casein and other protein sources.

It is clear from the available literature that the poor taste and organoleptic properties of most commonly available nutrition formulas are the principal reason for their poor palatability. Thus, patients generally will not comply with programs to consume nutritionally adequate quantities of many of the amino acid-containing formulas or fish oil-containing nutrition formulas. However, the present invention allows one to significantly improve the taste characteristics and palatability of nutritional support compositions such that they can be effectively utilized orally.

SUMMARY OF THE INVENTION

Orally-ingestible nutrition compositions having an improved taste comprise a low pH form of an amino acid selected from the group consisting of arginine, valine and other compounds associated with the synthesis of polyamines. The objectionable bitter taste of these amino acids is improved by their use or conversion in situ to a low pH (i.e. less than 7, preferably less than 6) salt or other form, such as for example, phosphates, citrates, malates, tartrates, acetates, fumarates, adipates, lactates, hydrates and other ionic species and mixtures thereof. Preferred compositions comprise arginine phosphate or mixture of arginine phosphate and arginine citrate. The compositions also preferably comprise a nucleobase source, such as RNA, and polyunsaturated fatty acid, such as omega-3 and omega-6 polyunsaturated fatty acids from fish oil; the fatty acids preferably being encapsulated.

The compositions can be in any form such as a dry powder or aqueous based liquid. The compositions have a pH of about 3 to 7 and provide in one unit dose an energy supply from about 750 to 3500K cal/day. The compositions are relatively pleasant tasting and suitable for oral ingestion.

DETAILED DESCRIPTION

The present invention relates to orally-ingestible nutrition compositions having an improved taste and palatability comprising a low pH form of an amino acid such as those selected from the group consisting of arginine, valine and other compounds associated with the synthesis of polyamines and mixtures thereof. These compositions effectively overcome the objectionable taste and organoleptic properties of amino acid-containing nutrition composition.

The amino acids used in this invention are extremely bitter and objectionable at alkaline pH. The taste of nutrition compositions containing these amino acids are dramatically improved by using a low pH form of the amino acids or conversion thereto in situ with food grade acids. Any low pH form, such as a salt or ionic species, of the amino acid is useful in this invention provided that it is physiologically acceptable and does not have an objectionable taste. Low pH forms include acid addition salts of food grade acids such as phosphoric, citric, adipic, tartaric, acetic, fumaric, malic and lactic acid and the like. They also include salts and ionic species having an acidic aqueous pH of less than 7 or formed in situ at acidic pH. Examples of suitable salts of amino acids for this invention include, but are not limited to, phosphates, citrates, acetates, malates, tartrates, fumurates, adipates, lactates, hydrates and the like and mixtures thereof. Examples of suitable ionic species include, but are not limited to, the cations of the amino acid salts listed above.

The preferred low pH forms are the ions and salts of the phosphates or mixtures of said phosphates and citrates. The most preferred salts for use in this invention are phosphates of arginine and other compounds associated with the synthesis of polyamines. The term "compound associated with the synthesis of polyamines" as used herein is intended to include, but not limited to arginine, arginine precursors, ornithine and the like. Arginine has been shown to enhance host defense mechanisms. This is evidenced by increased blastogenesis of lymphocytes in response to mitogens in animals and humans; reduced tumor appearance and incidence; increased survival in animals; and increased receptivity of cells to lymphokines.

The amount of arginine component to be supplied may vary within wide ranges, depending on inter alia the desired treatment, the subject to be treated and the subject's needs. Thus, where the subject to be treated is an adult person (typically of ca. 60 to 75 kg body weight) a satisfactory immunostimulatory response is, in general, obtained with compositions formulated to allow a daily administration of 3 to 40 grams, preferably 10 to 30 grams, most preferably 15 to 22 grams of arginine. Ornithine and/or other compounds associated with the synthesis of polyamines, may be substituted on a 1:1 molar ratio for arginine, or used in combination with arginine.

The low pH form of the amino acids of this invention, such as arginine phosphate for example, can be prepared by dissolving the arginine (free base) in water at a concentration slightly under saturation (i.e. 15% w/w). A food grade acid such as concentrated phosphoric acid is added and the pH adjusted to less than or about 4. This solution can then be used in its current state or mixed with a carrier, such as maltodextrin and/or dried by a variety of techniques, such as freeze drying, spray drying, vacuum drying or the like.

The compositions of this invention can contain varying amounts of the low pH form of amino acid, preferably from about 0.1 to about 20% by solid weight, more preferably from about 3 to about 10%. Preferred compositions comprise from about 3 to about 50 grams of the low pH form of amino acid in each daily dosage unit.

Nutrition compositions of the present invention preferably comprise a nucleobase source and polyunsaturated fatty acids. Nucleobase sources suitable for use in the compositions of the invention comprise or consist of natural nucleobases, nucleosides, nucleotides, RNA, DNA, equivalents thereof and/or mixtures comprising one or more of these compounds.

Natural nucleobases include the purines, adenine and guanine, as well as the pyrimidines cytosine, thymine and uracil. Where the nucleobase source is in the form of free nucleobases, it is preferably uracil.

Natural nucleosides include the ribose nucleosides adenosine, guanosine, uridine and cytidine and the deoxyribose nucleosides deoxyadenosine, deoxyguanosine, deoxythymidine and deoxycytidine.

Natural nucleotides include phosphate esters of natural nucleosides, such as the monophosphates adenylate (AMP), guanylate (GMP), uridylate (UMP), cytidylate (CMP), deoxythymidylate (dTMP) deoxycytidylate (dCMP), and diphosphates and triphosphates of natural nucleosides such as ADP and ATP.

A purified nucleobase source, such as yeast, is preferred. However, other sources such as meat and the like may be used.

The amount of nucleobase source to be administered will depend on the type of treatment desired, the subject to be treated and the like. Thus, where the subject to be treated is an adult person, a satisfactory immunostimulatory response is, in general, obtained with compositions of the invention formulated to allow a daily administration of from 0.1 to 4.0 grams, preferably 1 to 3 grams, most preferred from 1.25 to 2.5 grams of RNA, or an equivalent amount of another nucleobase source. For the purpose of this invention one weight unit of nucleobase is regarded to be equivalent with 2.5 to 3.0 weight units of RNA, DNA, nucleosides or nucleotides.

Polyunsaturated fatty acids are well known in the art as those having two or more double bonds per molecule and are available from a variety of plant, animal and synthetic sources. Preferred polyunsaturated fatty acids (PUFA) for use according to this invention include the omega-3 PUFA and omega-6 PUFA and mixtures thereof. Examples of omega-3 PUFA particularly appropriate for use in the compositions of the invention include eicosapentaenoic acid (EPA) and docosahexaenoic acid (DHA). Suitable sources for such omega-3 PUFA are known. They include linseed oil, canola oil and fish oils such as menhaden oil, salmon oil, mackeral oil, cod oil, herring oil, sardine oil, capelin oil and blends thereof.

The amount of omega-3 PUFA to be administered will inter alia depend on the type of treatment, the subject to be treated and the like. Thus, where the subject to be treated is an adult person a satisfactory immunostimulatory response is, in general, obtained with compositions of the invention formulated to allow a daily dosage of from about 0.1 to 20 grams, preferably from 0.1 to 15 grams, most preferably from 0.15 to 10.0 grams of omega-3 fatty acids.

Examples of omega-6 PUFA particularly appropriate for use according to the invention include linoleic acid and arachidonic acid (ETA), linoleic acid being most preferred. Examples of suitable omega-6 PUFA sources are known in the art. They include vegetable oils. Preferred are omega-6 PUFA sources having a high linoleic acid content such as safflower oil, sunflower oil, soya oil, cotton oil and corn oil.

The amount of omega-6 PUFA to be supplied will inter alia depend on the type of treatment, the subject to be treated and the like. Typically, the compositions of the invention will provide for a daily dosage of from 0.1 to 20 grams, preferably 0.15 to 15 grams, most preferably 0.5 to 10 grams of omega-6 PUFA.

The omega-3 and the omega-6 PUFA useful in this invention may be in the free acid form or in a form suitable for the physiological supply of omega-3 or omega-6 PUFA, such as the triglyceride form.

In preferred compositions of this invention the polyunsaturated fatty acids are encapsulated to mask the taste and to improve shelf stability.

Fish oils are easily oxidized and several compounds in oxidized oils have been associated with cellular damage and disease. Unsaturated fatty acids in the presence of appropriate free radical initiators react readily with atmospheric oxygen and undergo autoxidation. The process begins with the loss of hydrogen radicals from methylene groups of the cis 1, 4 pentadiene systems in the unsaturated fatty acid molecule and may be initiated by transition metals, ultraviolet light, enzymes, and/or heat. After an initial induction period, the rate of oxygen absorption increases exponentially. The fatty acid free radicals are highly reactive and combine with oxygen to form peroxy radicals. These in turn abstract hydrogen from additional unsaturated fatty acid molecules to form fatty acid hydroperoxides, the primary products of autoxidation. Hydroperoxides are very unstable and breakdown to produce many types of secondary products. The autoxidation of oils causes oxidation and the development of unpleasant flavors and odor in food. Hydroperoxides are tasteless; however, their decomposition products, saturated and unsaturated aldehydes, ketones, acids and other oxidative compounds impart repulsive flavors and odors. Oxidation can be detected at an early stage because the small molecular weight compounds formed possess very low odor thresholds; only a few parts per million or parts per billion are necessary to impart an unacceptable odor and flavor to fish oils.

Inhibition of oxidation of fish oils is achieved by limiting their exposure to oxygen and their contact with metallic ions. This is preferably achieved by extracting fish oil from fish using cold temperatures, antioxidants (Vitamin E & C, BHA, BHT, TBHQ) and the use of nitrogen to replace oxygen. After the fish oil is extracted, the careful control and encapsulation and packaging will ensure product with long-term stability and acceptable taste. Methods for encapsulation of oils, such as fish oils, flavor oils and the like, are known in the art using a variety of natural and synthetic polymers. Any of the encapsulation methods known in the art are useful according to this invention. For example, U.S. Pat. No. 3,897,361 describes a process for producing microcapsules of a hydrophobic oil and this disclosure is herein incorporated by reference.

The compositions of the invention are particularly suitable for oral ingestion, but may also be administered to the gastro-intestinal tract via feeding tube. The compositions are preferably in aqueous form or in a dry powder form, whereby the powder is conveniently added to water prior to use. The powder form of the composition avoids any thermoprocessing of the composition such as pasteurization and the like. Packaging of the composition is preferably carried out under an oxygen free environment to give a product which has little oxidation. Suitable packaging may include for example steel or composite canisters or hermetically sealed packets, all of which are impermeable to oxygen. The packaged product is shelf stable for one year or more.

The compositions may optionally comprise vitamins, minerals, trace elements, flavorings, colorants, sweeteners and a variety of other ingredients useful in nutrition compositions. Sweeteners can include any of the natural or artificial sweetening agents known in the art, but preferably the sweetener is sucrose, fructose, maltodextrin or aspartame. It is preferred to use a whey protein in the composition which gives a stable uncoagulated composition over a wide pH range, preferably at about pH 3–7. Preferred flavorings for the compositions are the natural and artificial acid flavorings such as lemon, lime, orange, peach, pineapple and raspberry and the like.

The compositions of the present invention have a pH ranging from about 3 to about 7, more preferably from about 3 to about 6, most preferably from about 3 to about 5.

According to a preferred embodiment of the invention, the compositions are in the form of a complete diet used as the sole nutrition source which supplies all the required daily calories, nitrogen, fatty acids, vitamins, minerals and trace elements.

In general, the daily caloric amount to be supplied to an adult person by the compositions will range from about 750 to 3500 kcal/day, preferably from about 1000 to 2000 kcal/day. Depending on the patient's condition, e.g. for use against post-surgical trauma, it may be desirable to initially (for example from day 1 to 5) administer a hypocaloric daily amount and to increase the energy supply thereafter to meet the normal daily caloric requirements. The contribution of the nitrogen source, carbohydrate source and lipid source to the total daily caloric may vary within wide ranges. In preferred compositions of the invention the carbohydrate source provides for 40 to 70% of the total energy supply and, the nitrogen and fatty acid source each provides for 15 to 30% of the total energy supply of the composition.

Some examples of suitable nitrogen sources for the compositions of this invention include nutritionally acceptable proteins such as whey proteins, caseinates, and protein hydrolysates and the like. Suitable carbohydrate sources include for example maltodextrins, sucrose, fructose and the like. Suitable fatty acid sources include for example the triglycerides and the like. Preferred examples of triglyceride sources suitable for use in the composition of the invention include triglyceride oils supplying the desired amounts of omega-3 and omega-6 fatty acids and which are rich in the medium chain fatty acid residues (i.e. residues of $C_6$ to $C_{12}$ fatty acid) and/or mono-unsaturated fatty acid residues. Preferably the triglyceride source provides a balance between the various types of unsaturated fatty acids, in particular between polyunsaturated omega-3, polyunsaturated omega-6 and mono-unsaturated omega-9 fatty acids, to manipulate the eicosanoids produced. Suitable sources of such triglycerides are e.g. physical mixtures of LCT (long chain triglycerides) and MCT (medium chain triglycerides) or structured lipids.

The MCT and LCT suitable for use in the physical mixtures may be used in pure form or in the form of oils rich in MCT or LCT. The LCT sources, as stated earlier, are conveniently rich in essential fatty acid residues. Suitable MCT sources are e.g. vegetable oils, including kernel oils such as palm kernel oil, coconut oil, balassu oil, cohune oil, tucum oil and fractions thereof.

Preferred compositions of the invention comprise triglycerides providing for a daily supply of from 1 to 30 grams, preferably of 2 to 20 grams, most preferred of 7 to 16 grams of medium chain fatty acids, in particular of lauric acid.

Particularly preferred compositions of the invention comprise triglycerides providing a daily supply of from 1 to 30 grams, preferably from 5 to 25 grams, most preferably from 5 to 20 grams of mono-unsaturated fatty acids. Suitable sources for mono-unsaturated fatty acids provide omega-9 mono-unsaturated fatty acids and are rich in oleic acid. Examples of such sources comprise olives, canola, safflower (hybrids) and sunflower (hybrids).

Examples of vitamins suitable for incorporation in the composition of the invention include vitamin A, vitamin D, vitamin E, vitamin K, vitamin C, folic acid, thiamin, riboflavin, vitamin $B_6$, vitamin $B_{12}$, niacin, biotin and pantothenic acid in pharmaceutically acceptable form.

Examples of mineral elements and trace elements suitable for incorporation in the composition of the invention include sodium, potassium, calcium, phosphorous, magnesium, manganese, copper, zinc, iron, selenium, chromium and molybdenum in pharmaceutically acceptable form.

A particularly preferred nutrition composition of the invention comprises:

a) about 3 to about 50 grams of a low pH form of arginine;

b) about 0.1 to about 4 grams of RNA;

c) about 0.1 to about 20 grams of omega-3 polyunsaturated fatty acids;

d) about 0.1 to about 20 grams of omega-6 polyunsaturated fatty acids.

The compositions of this invention are particularly suitable for use in patients who suffer from depressed host defense mechanisms, e.g. in patients who suffer from depressed host defense mechanisms as a result of post-surgical trauma, cancer, chemotherapy/radiation therapy, sepsis, trauma, burns, immunosuppressive drug therapy, malnutrition, transfusion induced immunosuppression and the like. It has indeed been observed that the body, when under severe stress, cannot readily mobilize the nutrients necessary to secure a normal function. The administration of the composition of the invention helps to maintain, restore and enhance the immune function where desired. The immune system reacts surprisingly quick and favourable to the administration of the composition of the invention. Such compositions may accordingly be employed to enhance a depressed host defense mechanism, to restore a normal immune function in a human with a deficient immune response, to enhance the development of the immune system in a developing human, to enhance a senescent immune system of a human and the like.

The invention accordingly also provides the compositions of the invention for use in a method of maintaining or stimulating the immune system of a patient, in need of such treatment. Further, the invention provides a method for improving the taste and organoleptic quality of an orally-ingestible nutrition composition containing amino acid which comprises incorporating therein a low pH form of an amino acid according to the invention.

The following examples are presented to further illustrate this invention. The examples are intended in an illustrative sense and not a limitative sense. The invention includes the embodiments shown and described herein and equivalents thereof.

EXAMPLE I

Compositions within the scope of the present invention were prepared by dissolving arginine in water to form solutions comprising 15% by weight arginine. The pH of the solutions were adjusted from the original pH of approximately 10 to various pHs ranging from pH 3 to pH 7 using concentrated phosphoric acid. The solutions were then evaluated for taste and sensory attributes and rated on a scale of 0 to 3 (0–1=fully acceptable; 2=objectionable; 3=not edible). The results of this evaluation are presented in Table I below:

TABLE I

| Arginine Solution | pH | Rating | Sensory Response |
|---|---|---|---|
| A | 10 | 3 | Extremely bitter; offensive flavor |
| B | 7 | 2 | Very bitter |
| C | 6 | 1 | Slight bitterness |
| D | 5 | 1 | Slight bitterness |
| E | 4 | 0 | No bitterness; slightly acidic |
| F | 3 | 1 | No bitterness; acidic |

The results demonstrate that at acidic pH below 7 the taste and sensory attributes of arginine is significantly improved as arginine phosphate.

EXAMPLE II

A dry powder nutrition composition within the scope of this invention was prepared by blending the ingredients and packaging them in a nitrogen atmosphere (oxygen-free) to yield a final composition having the following formulation:

| Ingredient | Amount (Wt. %) |
|---|---|
| Fructose | 37.0 |
| Whey Protein Concentrate | 19.0 |
| Encapsulated Fish Oil | 17.0 |
| Oil | 8.0 |
| Citric Acid | 7.0 |
| Vitamins/Minerals/RNA | 6.0 |
| L-Arginine | 5.0 |
| Flavors (orange-pineapple) | 1.0 |

One-half cup of this powder composition can be reconstituted in 8 fluid ounces of water or other liquid to yield a composition having a pH from about 3–5. The composition has an orange-pineapple flavor and no bitterness.

EXAMPLE III

A liquid nutrition composition according to the invention was prepared having the following formulation:

| Ingredient | Amount (Wt. %) |
|---|---|
| Deionized Water | 78.0 |
| Sugar | 14.0 |
| Whey Protein Concentrate | 4.0 |
| L-Arginine | 2.5 |
| Vitamins/Minerals | 0.9 |
| Phosphoric Acid | 0.3 |
| Citric Acid | 0.2 |
| Flavor/Color | 0.1 |

The pH of the composition is less than 4.0 and the combination of phosphoric and citric acids is used to avoid the astringency caused by too much citric acid.

EXAMPLE IV

A nutrition bar composition according to this invention was/ prepared having the following formulation:

| Ingredient | Amount | |
|---|---|---|
| Vitamin A | 5000.0 | IU |
| Vitamin $D_3$ | 400.0 | IU |
| Vitamin E | 50.0 | mg |
| Vitamin $K_1$ | 0.1 | mg |
| Vitamin $B_1$ | 2.4 | mg |
| Vitamin $B_2$ | 2.6 | mg |
| Vitamin $B_6$ | 2.2 | mg |
| Niacin | 30.0 | mg |
| Pantothenic Acid | 10.0 | mg |
| Vitamin C | 120.0 | mg |
| Biotin | 0.225 | mg |
| Folic Acid | 400.0 | mg |
| Vitamin $B_{12}$ | 9.0 | mg |
| B-Carotene | 1.5 | mg |
| Calcium | 250 | mg |
| Phosphorus | 250 | mg |
| Magnesium | 200 | mg |
| Sodium | 15 | mg |
| Potassium | 150 | mg |
| Iron | 15.0 | mg |
| Zinc | 22.5 | mg |
| Manganese | 3.5 | mg |
| Copper | 2.5 | mg |
| Fluoride | 2.5 | mg |
| Molybdenum | 300 | mg |
| Chromium | 150 | mg |
| Iodine | 100 | mg |
| Selenium | 50 | mg |

-continued

| Ingredient | Amount | |
|---|---|---|
| RNA-yeast extract | 2.0 | g |
| L-Arginine-phosphate | 4.0 | g |

(Daily serving size is 60 grams)

EXAMPLE V

A pudding composition according to this invention can be prepared by blending 13.8 oz. of a pudding mix (lemon DELMARK QUICK$^R$ pudding mix) with 8 oz. of arginine-phosphate. Two quarts of milk are then added and mixed. The pudding composition is kept refrigerated until served. The pH of the pudding is about 4–5. A 3 oz. serving of the pudding provides 5 grams of arginine.

EXAMPLE VI

A yogurt composition according to this invention can be prepared by thoroughly mixing 2.0 oz. of arginine phosphate with 1 cup of fruit preparation. 1 quart of plain yogurt is added and lightly mixed. A 4 oz. serving provides 5 grams of arginine.

EXAMPLE VII

Dry powder nutrition compositions were prepared having the following formulations:

| | Amount (Wt. %) Sample | | |
|---|---|---|---|
| Ingredients | A | B | C |
| Fructose | 45.0 | 38.0 | 41.0 |
| Whey Protein Concentrate | 19.0 | 19.0 | 19.0 |
| Encapsulated Fish Oil | 17.0 | 17.0 | 17.0 |
| Oils | 8.0 | 8.0 | 8.0 |
| Citric Acid | 0 | 7.0 | 4.0 |
| Vitamins/Minerals/RNA | 5.0 | 5.0 | 5.0 |
| L-Arginine | 5.0 | 5.0 | 5.0 |
| Flavors | 1.0 | 1.0 | 1.0 |

Liquid samples of the above compositions were prepared by mixing 61 grams of the powder with 8 fluid oz. of water. Sample A had a pH of 9.6. The pH of Sample B and Sample C were 4.4 and 5.6, respectively. Sensory evaluations were conducted on the three samples using a panel of 30 participants who rated the taste of the samples on a scale of 1–3 (1=most preferred taste; 3=least preferred taste). Rank sum scores for each of the samples were calculated and analyzed using the Friedman test and Fisher's least. significant difference procedures. The results are presented in Table II below:

TABLE II

| Sample | pH | Rank Sum Score |
|---|---|---|
| A | 9.6 | 77 |
| B | 4.4 | 56 |
| C | 5.6 | 47 |

The results show that Sample B and Sample C having the lower Rank Sum Scores were significantly preferred over Sample A.

EXAMPLE VIII

A dry powder nutrition composition was prepared as in Example II. The pH of this sample was 4.4.

A liquid nutrition composition was prepared having the following composition:

| Ingredient | Amount (% Weight) |
|---|---|
| Deionized Water | 76.0 |
| Maltodextrin | 14.0 |
| Caseinate | 5.0 |
| Arginine | 1.0 |
| MCT/Sunflower Oil | 1.5 |
| Fish Oil | 1.0 |
| Citric Acid | 0.4 |
| Vitamins/Minerals/RNA | 1.1 |

The pH of this sample was 7.3

Sensory evaluations were conducted on the two samples using a panel of 6 participants. Panelist evaluated the samples for overall liking. The nutritional composition having a pH of 4.4 was significantly preferred over the composition having a pH of 7.3.

We claim:

1. An orally-ingestible nutrition composition having an improved taste and palatability comprising a carbohydrate source providing from 40 to 70%, a nitrogen source providing from 15 to 30% and a fatty acid source providing from 15 to 30% of the total energy supply of said composition, wherein said composition comprises a low pH form of an amino acid having an aqueous pH of less than 6 at a concentration of about 0.1 to about 20% by solid weight, said low pH form being selected from the group consisting of phosphates, citrates, acetates, tartrates, fumarates, adipates, lactates, hydrates and mixtures thereof, wherein said amino acid is selected from the group consisting of arginine, valine and ornithine and wherein said composition is a dry powder.

2. The nutrition composition of claim 1 wherein said amino acid is arginine.

3. The nutrition composition of claim 1 wherein said low pH form is arginine phosphate.

4. The nutrition composition of claim 1 wherein said low pH form is a mixture of arginine phosphate and arginine citrate.

5. The nutrition composition of claim 1 comprising a nucleobase source and polyunsaturated fatty acid.

6. The nutrition composition of claim 5 wherein said fatty acid is encapsulated.

7. The nutrition composition of claim 6 wherein said nucleobase source is ribonucleic acid.

8. The nutrition composition of claim 6 wherein said fatty acid comprises omega-3 and omega-6 polyunsaturated fatty acids.

9. The composition of claim 6 wherein said fatty acid is derived from fish oil.

10. The nutrition composition of claim 5 comprising:

a) about 3 to about 50 grams of a low pH form of arginine;

b) about 0.1 to about 4 grams of ribonucleic acid;

c) about 0.1 to about 20 grams of omega-3 polyunsaturated fatty acids;

d) about 0.1 to about 20 grams of omega-6 polyunsaturated fatty acids.

11. The nutrition composition of claim 6 providing in one unit dose an energy supply from about 750 to about 3500K cal/day.

12. The nutrition composition of claim 1 comprising one or more natural or artificial flavoring selected from the group consisting of lemon, lime, orange, peach, pineapple and raspberry.

* * * * *